US011361602B2

(12) United States Patent
Chen et al.

(10) Patent No.: US 11,361,602 B2
(45) Date of Patent: Jun. 14, 2022

(54) METHOD FOR CALCULATING TREAD FREQUENCY OF BICYCLE, WEARABLE DEVICE, AND STORAGE MEDIUM

(71) Applicant: Huawei Technologies Co., Ltd., Shenzhen (CN)

(72) Inventors: Yixin Chen, Shenzhen (CN); Chen Dong, Shenzhen (CN); Xiaohan Chen, Shenzhen (CN); Yu Wang, Beijing (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 0 days.

(21) Appl. No.: 17/046,939

(22) PCT Filed: Apr. 13, 2018

(86) PCT No.: PCT/CN2018/083031
§ 371 (c)(1),
(2) Date: Oct. 12, 2020

(87) PCT Pub. No.: WO2019/196106
PCT Pub. Date: Oct. 17, 2019

(65) Prior Publication Data
US 2021/0049842 A1 Feb. 18, 2021

(51) Int. Cl.
*G07C 5/08* (2006.01)
*G01P 1/12* (2006.01)
*G01P 15/18* (2013.01)

(52) U.S. Cl.
CPC .............. *G07C 5/085* (2013.01); *G01P 1/127* (2013.01); *G01P 15/18* (2013.01)

(58) Field of Classification Search
CPC ......... G07C 5/085; G01P 1/127; G01P 15/18; B62J 45/413; B62J 45/414
See application file for complete search history.

(56) References Cited

U.S. PATENT DOCUMENTS

| 2007/0054778 A1* | 3/2007 | Blanarovich ...... A63B 24/0062 482/8 |
| 2013/0205896 A1* | 8/2013 | Baechler ................. G01P 1/023 73/493 |

(Continued)

FOREIGN PATENT DOCUMENTS

| CN | 101634659 A | 1/2010 |
| CN | 102811285 A | 12/2012 |

(Continued)

OTHER PUBLICATIONS

XP011574279, Xu, J., et al., "Integrated inertial sensors and mobile computing for real-time cycling performance guidance via pedaling profile classification," IEEE Journal of Biomedical and Health Informatics (vol. 19, Issue: 2, Mar. 2015), 6 pages.

(Continued)

*Primary Examiner* — Manuel L Barbee
(74) *Attorney, Agent, or Firm* — Conley Rose, P.C.

(57) ABSTRACT

A method for calculating a tread frequency of a bicycle includes obtaining a first state of an acceleration signal in a first time window, determining a feature point set from the acceleration signal when the first state includes a riding state, where time distribution of a feature point in the feature point set meets a preset periodic distribution condition, and amplitude meets a physical rule, determining that the first state is the riding state when a feature point subset in the feature point set meets a preset reasonableness condition, and calculating, based on the feature point subset, a quantity of circles and a tread frequency that are in the first time window.

20 Claims, 14 Drawing Sheets

(56) References Cited

U.S. PATENT DOCUMENTS

| | | |
|---|---|---|
| 2015/0087995 A1 | 3/2015 | Murai |
| 2015/0099945 A1 | 4/2015 | Hawkins, III et al. |
| 2016/0154952 A1 | 6/2016 | Venkatraman et al. |
| 2016/0259905 A1 | 9/2016 | Park et al. |
| 2017/0003311 A1* | 1/2017 | Lay ...................... B62J 45/414 |
| 2017/0007166 A1* | 1/2017 | Roovers ............... A61B 5/0205 |
| 2017/0097375 A1* | 4/2017 | Liu ........................... G01P 3/44 |
| 2017/0151989 A1 | 6/2017 | Daniels |
| 2017/0328931 A1 | 11/2017 | Zhang et al. |
| 2018/0234661 A1 | 8/2018 | Tsukahara et al. |
| 2021/0276654 A1* | 9/2021 | Wang ................... B62J 45/413 |

FOREIGN PATENT DOCUMENTS

| | | |
|---|---|---|
| CN | 203001786 U | 6/2013 |
| CN | 104077795 A | 10/2014 |
| CN | 105183158 A | 12/2015 |
| CN | 205409997 U | 8/2016 |
| CN | 105935289 A | 9/2016 |
| CN | 205548573 U | 9/2016 |
| CN | 106139559 A | 11/2016 |
| CN | 106663343 A | 5/2017 |
| CN | 106950398 A | 7/2017 |
| CN | 106996985 A | 8/2017 |
| CN | 107025370 A | 8/2017 |
| WO | 2017057037 A1 | 4/2017 |

OTHER PUBLICATIONS

XP032462884, Zhang, Y., et al., "Monitoring Walking and Cycling of Middle-Aged to Older Community Dwellers Using Wireless Wearable Accelerometers," 2012 Annual International Conference of the IEEE Engineering in Medicine and Biology Society, 4 pages.
XP035156504, Perianu, R., et al., "A performance analysis of a wireless body-area network monitoring system for professional cycling," Personal and Ubiquitous Computing, vol. 17, 2013, 13 pages.

\* cited by examiner

METHOD FOR CALCULATING TREAD FREQUENCY OF BICYCLE, WEARABLE DEVICE, AND STORAGE MEDIUM

CROSS-REFERENCE TO RELATED APPLICATIONS

This application is a U.S. National Stage of International Patent Application No. PCT/CN2018/083031 filed on Apr. 13, 2018, which is hereby incorporated by reference in its entirety.

TECHNICAL FIELD

This application relates to the field of motion apparatuses, and in particular, to a method for calculating a tread frequency of a bicycle, a wearable device, and a storage medium.

BACKGROUND

An accelerometer is usually mounted on a rotation carrier, for example, a bicycle wheel to obtain a rotational speed or a speed of the rotation carrier, for example, the bicycle wheel. A centripetal acceleration of the carrier during rotation is extracted based on an output signal of the accelerometer, and the rotational speed of the rotation carrier is obtained based on a relationship between a centripetal acceleration, a rotational speed, and a rotation radius. Alternatively, a periodic signal output by the accelerometer is detected in time domain and frequency domain. A rotation period or a rotation frequency of the carrier is obtained through calculation performed based on the periodic signal, to obtain the rotational speed or the speed of the rotation carrier. However, the accelerometer mounted on a bicycle needs to be independently mounted on the rotation carrier because the accelerometer is not a wearable device, and can transmit the output signal of the accelerometer only through communication, for example, Bluetooth. Therefore, the accelerometer is inconvenient for use.

A sensor, for example, an accelerometer is configured in a current wearable device. When a user wears the wearable device on a foot, the wearable device may calculate a current quantity of steps of the user based on a signal output by the sensor. However, the wearable device cannot be used to calculate a tread frequency or identify a riding state.

SUMMARY

This application provides a method for calculating a tread frequency of a bicycle, a wearable device, and a storage medium, to resolve a problem in the prior art that a wearable device cannot calculate a tread frequency or automatically identify a riding state.

A first aspect of this application provides a method for calculating a tread frequency of a bicycle. The method includes:
obtaining a first state of an acceleration signal in a first time window;
when it is determined that the first state includes a riding state, determining a feature point set from the acceleration signal, where time distribution of a feature point in the feature point set meets a preset periodic distribution condition, and amplitude meets a physical rule;
when it is determined that a feature point subset in the feature point set meets a preset reasonableness condition, determining that the first state is the riding state; and
calculating, based on the feature point subset, a quantity of circles and a tread frequency that are in the first time window.

Compared with the prior art, in a solution provided in this application, when it is determined that the first state includes the riding state, the feature point set whose time distribution of the feature point meets the preset periodic distribution condition and whose amplitude meets the physical rule is determined from the acceleration signal. Then, when it is further determined that the feature point subset in the feature point set meets the preset reasonableness condition, it is determined that the first state is the riding state, and then the quantity of circles and the tread frequency that are in the first time window are calculated based on the feature point subset. By using this solution, after a user wears a wearable device on a leg, a quantity of circles and a tread frequency that are of a rotation carrier can be accurately calculated without a need to pre-obtain a parameter of the rotation carrier (for example, the bicycle) or mount the wearable device on the rotation carrier.

In some possible designs, the obtaining a first state of an acceleration signal in a first time window includes:
obtaining a three-axis acceleration signal;
calculating a combined acceleration of acceleration signals, of all axes, in the three-axis acceleration signal, where the combined acceleration is a square root of a sum of squares of a three-axis acceleration; and
determining the first state based on the combined acceleration, where the first state of the acceleration signal in the first time window may be a static state, a running state, a walking state, the riding state, or another state, and the first state is determined based on the combined acceleration, so that a state of the three-axis acceleration signal in the first time window can be preliminarily determined and screened.

In some possible designs, the feature point set includes a maximum value point set and a minimum value point set. Both time distribution of a maximum value point in the maximum value point set and time distribution of a minimum value point in the minimum value point set meet the preset periodic distribution condition, and the amplitude meets the related physical rule. This means that maximum value points and minimum value points are reasonable to be used to subsequently calculate the quantity of circles and the tread frequency.

In some possible designs, the determining a feature point set from the acceleration signal includes:
determining a first maximum value point set and a first minimum value point set from the acceleration signal;
calculating a time ratio and an amplitude ratio, of a first minimum value point and a second minimum value point, relative to a first maximum value point, where the first maximum value point is a maximum value point in the first maximum value point set, both the first minimum value point and the second minimum value are minimum value points in the first minimum value point set, and the first minimum value and the second minimum value are extreme value points adjacent to the first maximum value point; and
when the time ratio falls within a first value range and the amplitude ratio falls within a second value range, determining that time distribution of the first maximum value point meets the preset reasonableness condition, and obtaining the maximum value point set and the minimum value point set, where optionally, a preset threshold or an adaptive threshold may be further set to determine reasonableness of a maximum value point in the maximum value point set.

In some possible designs, the time ratio is $[t(x)-t(y1)]/[t(y2)-t(x)]$, and the amplitude ratio is $[acc\_f(x)-acc\_f(y1)]/[acc\_f(y2)-acc\_f(x)]$.

In the foregoing, $t(x)$ is a time point corresponding to the first maximum value point x1, $t(y1)$ is a time point corresponding to the first minimum value point y1, $t(y2)$ is a time point corresponding to the second minimum value point y2, $acc\_f(x)$ represents an amplitude value, of the acceleration signal, at x, $acc\_f(y1)$ represents an amplitude value, of the acceleration signal, at y1, and $acc\_f(y2)$ represents an amplitude value, of the acceleration signal, at y2. If filtering processing is performed on the acceleration signal, when the time ratio and the amplitude ratio are calculated, $acc\_f(x)$, $acc\_f(y1)$, and $acc\_f(y2)$ are all amplitude values of an acceleration signal obtained after the filtering processing. If the filtering processing is not performed on the acceleration signal, when the time ratio and the amplitude ratio are calculated, $acc\_f(x)$, $acc\_f(y1)$, and $acc\_f(y2)$ are all amplitude values of the original acceleration signal. This is not specifically limited in this application.

In some possible designs, after the obtaining the maximum value point set and the minimum value point set, the method further includes:
selecting a group of maximum value points from the maximum value point set; and
determining reasonableness of the group of maximum value points based on the preset reasonableness condition, where the preset reasonableness condition includes at least one of the following items:
a first ratio of an average value of the combined acceleration to a quantity of circles is greater than a first threshold; or
a first standard deviation of a time interval between adjacent maximum value points is less than a second threshold; or
a second ratio of a quantity of valid maximum value points to a quantity of original maximum value points is greater than a third threshold; or
a second standard deviation of a difference between amplitude values of maximum value points is less than a fourth threshold; or
a quantity of circles corresponding to a speed less than a first value is not greater than a first quantity of circles, a quantity of circles corresponding to a speed greater than the first value and less than a second value is not greater than a second quantity of circles, and the first quantity of circles is less than the second quantity of circles.

In some possible designs, after the determining that the first state of the acceleration signal is the riding state, the method further includes:
obtaining a second state of the acceleration signal in a second time window and a third state of the acceleration signal in a third time window, where the second time window, the third time window, and the first time window are adjacent and arranged in ascending order in time domain; and
correcting the third state based on the second state and the first state.

In some possible designs, the correcting the third state based on the second state and the first state includes:
when both the second state and the first state are non-riding states, and the third state is the riding state, correcting the state of the acceleration signal in the third time window to the non-riding state, and setting a quantity of circles in the third time window to 0; or
when both the second state and the first state are riding states, and the third state is a non-riding state, correcting the state of the acceleration signal in the third time window to the riding state.

In some possible designs, when both the second state and the first state are the riding states, and the third state is the non-riding state, the method further includes:
calculating the second quantity of circles based on a feature point set of the acceleration signal in the third time window; and
when a ratio of the second quantity of circles to the first quantity of circles falls within a third value range, determining that the state of the acceleration signal in the third time window is the riding state, and updating a recorded quantity of circles in the third time window to the second quantity of circles.

In some possible designs, the feature point set is an intersection point set, an intersection point in the intersection point set is an intersection point between the acceleration signal and an average value, and the average value is an average value of accelerations at all time points in the acceleration signal. Time distribution of these intersection points meets the preset periodic distribution condition, and amplitude meets the related physical rule.

In some possible designs, the acceleration signal is a gravity axis acceleration signal in the three-axis acceleration signal. There is almost no needed signal in an axis in a direction from the user's left to right. Therefore, the gravity axis acceleration signal in the three-axis acceleration signal may be used as the acceleration signal. It can be learned that only an acceleration signal in an axis in a gravity direction is used. This helps reduce impact caused by noise and reduce processing difficulty.

In some possible designs, smoothing processing is performed on the acceleration signal in a moving average filtering manner, and a high-frequency interference signal in the acceleration signal is removed in an infinite impulse response Butterworth low-pass filtering manner. A filtering manner includes but is not limited to the foregoing filtering manners, and another low-pass filtering manner may also be used.

A second aspect of this application provides a wearable device, and the wearable device has functions of implementing the method for calculating a tread frequency of a bicycle and implementing automatic detection of the riding state that are provided in the first aspect. The functions may be implemented by hardware, or may be implemented by hardware by executing corresponding software. The hardware or the software includes one or more modules corresponding to the foregoing functions, and the module may be software and/or hardware.

In a possible design, the wearable device includes:
the wearable device includes:
an obtaining module, configured to obtain a first state of an acceleration signal in a first time window; and
a processing module, configured to: when it is determined that the first state obtained by the obtaining module includes a riding state, determine a feature point set from the acceleration signal, where time distribution of a feature point in the feature point set meets a preset periodic distribution condition; when it is determined that a feature point subset in the feature point set meets a preset reasonableness condition, determine that the first state is the riding state; and calculate, based on the feature point subset, a quantity of circles and a tread frequency that are in the first time window.

In some possible designs, the obtaining module is configured to:
  obtain a three-axis acceleration signal;
  calculate a combined acceleration of acceleration signals, of all axes, in the three-axis acceleration signal; and
  determine the first state based on the combined acceleration.

In some possible designs, the feature point set includes a maximum value point set and a minimum value point set, both time distribution of a maximum value point in the maximum value point set and time distribution of a minimum value point in the minimum value point set meet the preset periodic distribution condition, and the amplitude meets the related physical rule.

In some possible designs, the processing module is configured to:
  determine a first maximum value point set and a first minimum value point set from the acceleration signal;
  calculate a time ratio and an amplitude ratio, of a first minimum value point and a second minimum value point, relative to a first maximum value point, where the first maximum value point is a maximum value point in the first maximum value point set, both the first minimum value point and the second minimum value are minimum value points in the first minimum value point set, and the first minimum value and the second minimum value are extreme value points adjacent to the first maximum value point; and
  when the time ratio falls within a first value range and the amplitude ratio falls within a second value range, determine that time distribution of the first maximum value point meets the preset reasonableness condition, and obtain the maximum value point set and the minimum value point set.

In some possible designs, the time ratio is $[t(x)-t(y1)]/[t(y2)-t(x)]$, and the amplitude ratio is $[acc\_f(x)-acc\_f(y1)]/[acc\_f(y2)-acc\_f(x)]$, where
  $t(x)$ is a time point corresponding to the first maximum value point x1, $t(y1)$ is a time point corresponding to the first minimum value point y1, $t(y2)$ is a time point corresponding to the second minimum value point y2, $acc\_f(x)$ represents an amplitude value, of the acceleration signal, at x, $acc\_f(y1)$ represents an amplitude value, of the acceleration signal, at y1, and $acc\_f(y2)$ represents an amplitude value, of the acceleration signal, at y2;

In some possible designs, after obtaining the maximum value point set and the minimum value point set, the processing module is further configured to:
  select a group of maximum value points from the maximum value point set; and
  determine reasonableness of the group of maximum value points based on the preset reasonableness condition, where the preset reasonableness condition includes at least one of the following items:
  a first ratio of an average value of the combined acceleration to a quantity of circles is greater than a first threshold; or
  a first standard deviation of a time interval between adjacent maximum value points is less than a second threshold; or
  a second ratio of a quantity of valid maximum value points to a quantity of original maximum value points is greater than a third threshold; or
  a second standard deviation of a difference between amplitude values of maximum value points is less than a fourth threshold; or
  a quantity of circles corresponding to a speed less than a first value is not greater than a first quantity of circles, a quantity of circles corresponding to a speed greater than the first value and less than a second value is not greater than a second quantity of circles, and the first quantity of circles is less than the second quantity of circles.

In some possible designs, after determining that the first state of the acceleration signal is the riding state, the processing module is further configured to:
  obtain, through the obtaining module, a second state of the acceleration signal in a second time window and a third state of the acceleration signal in a third time window, where the second time window, the third time window, and the first time window are adjacent and arranged in ascending order in time domain; and
  correct the third state based on the second state and the first state.

In some possible designs, the processing module is configured to:
  when both the second state and the first state are non-riding states, and the third state is the riding state, correct the state of the acceleration signal in the third time window to the non-riding state, and set a quantity of circles in the third time window to 0; or
  when both the second state and the first state are riding states, and the third state is a non-riding state, correct the state of the acceleration signal in the third time window to the riding state.

In some possible designs, when both the second state and the first state are the riding states, and the third state is the non-riding state, the processing module is further configured to:
  calculate the second quantity of circles based on a feature point set of the acceleration signal in the third time window; and
  when a ratio of the second quantity of circles to the first quantity of circles falls within a third value range, determine that the state of the acceleration signal in the third time window is the riding state, and update a recorded quantity of circles in the third time window to the second quantity of circles.

In some possible designs, the feature point set is an intersection point set, an intersection point in the intersection point set is an intersection point between the acceleration signal and an average value, and the average value is an average value of accelerations at all time points in the acceleration signal.

In some possible designs, the acceleration signal is a gravity axis acceleration signal in the three-axis acceleration signal.

According to a third aspect, this application provides a wearable device. The wearable device includes:
  at least one connected processor, a memory, and a transceiver.

The memory is configured to store program code, and the processor is configured to invoke the program code in the memory to perform the following operations:
  obtaining, by the transceiver, a first state of an acceleration signal in a first time window; and
  when it is determined that the first state obtained by the obtaining module includes a riding state, determining a feature point set from the acceleration signal, where time distribution of a feature point in the feature point set meets a preset periodic distribution condition; when it is determined that a feature point subset in the feature point set meets a preset reasonableness condition, determining that the first state is the riding state; and calculating, based on the feature point subset, a quantity of circles and a tread frequency that are in the first time window.

According to a fourth aspect, this application provides a computer-readable storage medium, and the computer-readable storage medium stores an instruction. When the instruction is run on a computer, the computer is enabled to perform the method in the first aspect.

According to a fifth aspect, this application provides a computer program product including an instruction, and when the computer program product runs on a computer, the computer is enabled to perform the method in the first aspect.

DESCRIPTION OF EMBODIMENTS

In the specification, claims, and accompanying drawings of this application, the terms "first", "second", and the like are intended to distinguish between similar objects, but do not necessarily indicate a specific order or sequence. It should be understood that data used in such a way are interchangeable in proper circumstances, so that embodiments described herein can be implemented in other orders than the order illustrated or described herein. In addition, the terms "include", "have", or any other variant thereof are intended to cover non-exclusive inclusion. For example, a process, a method, a system, a product, or a device that includes a series of steps or modules is not necessarily limited to the steps or modules that are expressly listed, but may include another step or module not expressly listed or inherent to the process, the method, the product, or the device. The module division in this application is merely logical division, and there may be another division during implementation in actual application. For example, a plurality of modules may be combined or integrated into another system, or some features may be ignored or not performed. In addition, the displayed or discussed mutual couplings or direct couplings or communication connections may be implemented through some interfaces. The indirect couplings or communication connections between the modules may be implemented in electric or another form, and this is not limited in this application. In addition, modules or sub-modules described as separate components may be or may not be physically separated, or may be or may not be physical modules, or may be grouped into a plurality of circuit modules. Objectives of the solutions of the embodiments of this application may be achieved by selecting some or all of the modules according to an actual requirement.

Figure 1A:
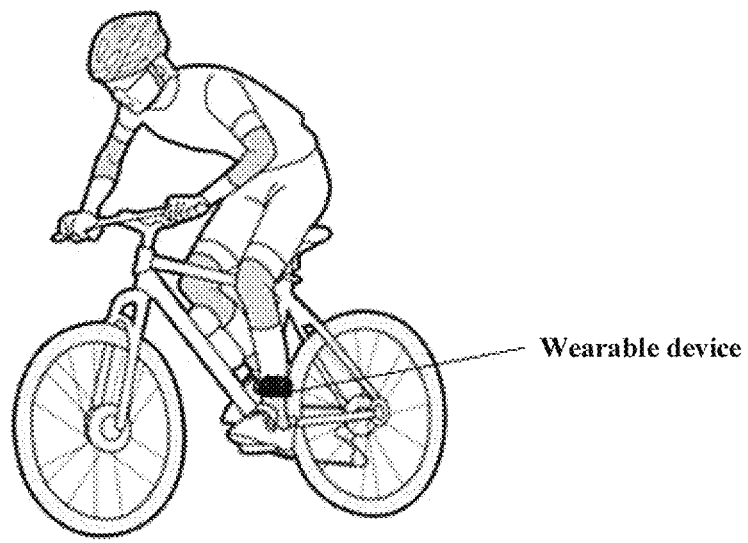
FIG. 1a is a schematic diagram of riding a bicycle by wearing a wearable device according to an embodiment of this application.
Figure 1B:
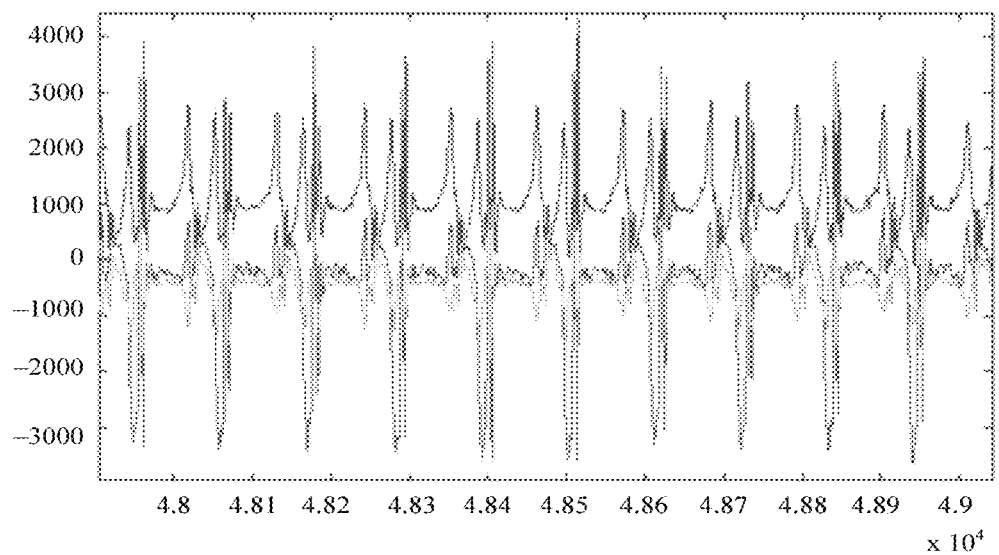
FIG. 1b is a schematic diagram of an original foot signal during waling collected by a wearable device according to an embodiment of this application.
Figure 1C:
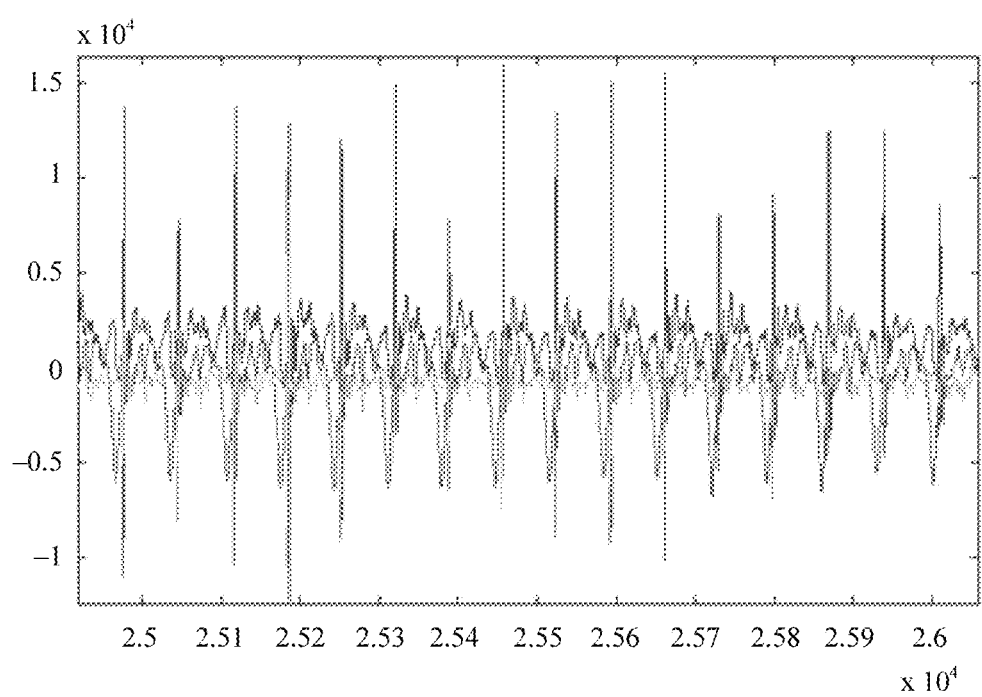
FIG. 1c is a schematic diagram of an original foot signal during running collected by a wearable device according to an embodiment of this application.

Embodiments of this application provide a method for calculating a tread frequency of a bicycle, a wearable device, and a storage medium that are applied to the field of motion apparatuses, for example, devices having rotation carriers such as the bicycle and an indoor stationary bicycle. This can resolve a problem in the prior art that a tread frequency cannot be accurately calculated through a wearable fabric in an existing mechanism. Detailed descriptions are provided below. FIG. 1a is a schematic diagram in which a user wearing a wearable device rides a bicycle. FIG. 1b shows an original foot signal during walking, of the user, collected by the wearable device in FIG. 1a. FIG. 1c shows an original foot signal during running, of the user, collected by the wearable device in FIG. 1a. In this application, a quantity of circles and a tread frequency are mainly calculated based on an original foot signal during running, for example, based on the original foot signal during running shown in FIG. 1c.

The wearable device in the embodiments of this application may be smart wearables, a sports foot band, a smart foot band, clothes, shoes, or the like.

Figure 2:
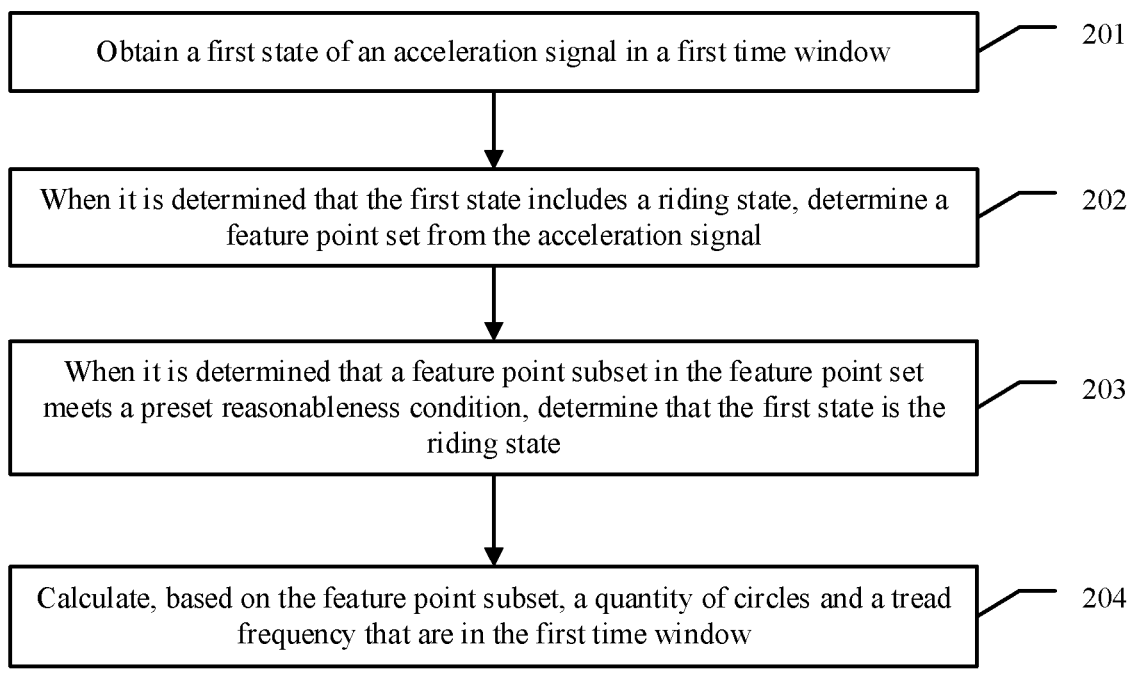
FIG. 2 is a flowchart of a method for calculating a tread frequency of a bicycle according to an embodiment of this application.

Referring to FIG. 2, the following describes an example of a method for calculating a tread frequency of a bicycle according to this application. The method includes the following steps.

201: Obtain a first state of an acceleration signal in a first time window.

The acceleration signal in this embodiment of this application may be sampled at a fixed sampling frequency. For example, if a length of a time window is 5 s, and the sampling frequency is 100 Hz, a signal in each axis has 500 time points and corresponding amplitude values (namely, acceleration values).

In some implementations, obtaining the first state of the acceleration signal in the first time window includes the following steps:

(a) Obtain a three-axis acceleration signal.

(b) Calculate a combined acceleration of acceleration signals, of all axes, in the three-axis acceleration signal.

The combined acceleration is a square root of a sum of squares of a three-axis acceleration. In other words, the combined acceleration is $sqrt(x^2+y^2+z^2)$, and sqrt represents calculating the square root.

(c) Determine the first state based on the combined acceleration.

Figure 3A:
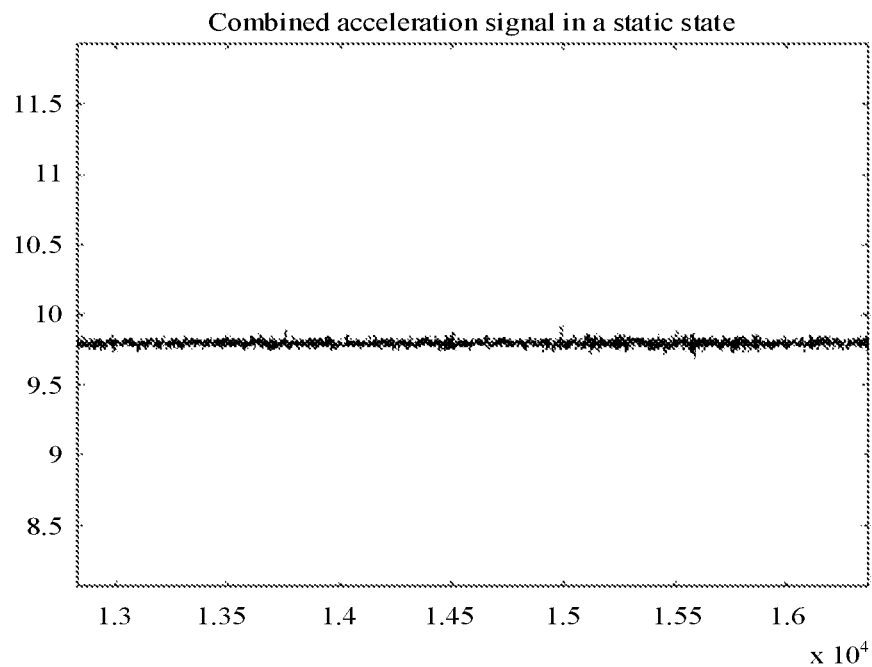
FIG. 3a is a schematic diagram of a combined acceleration signal in a static state, a combined acceleration signal in a walking state, and a combined acceleration signal in a running state according to an embodiment of this application.
Figure 3A:
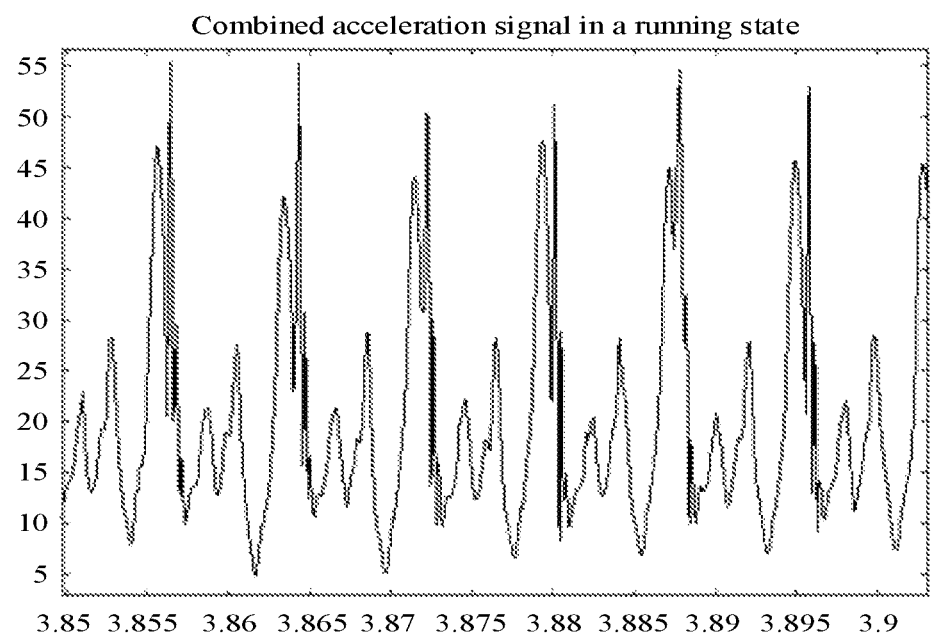
Figure 3A:
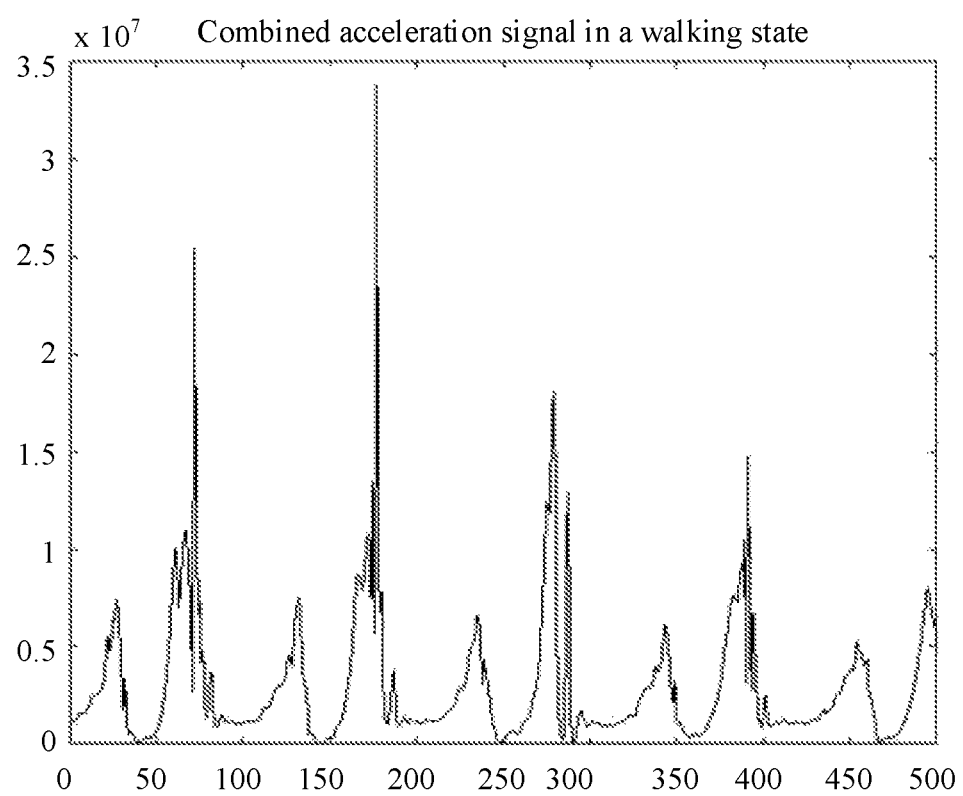
Figure 3B:
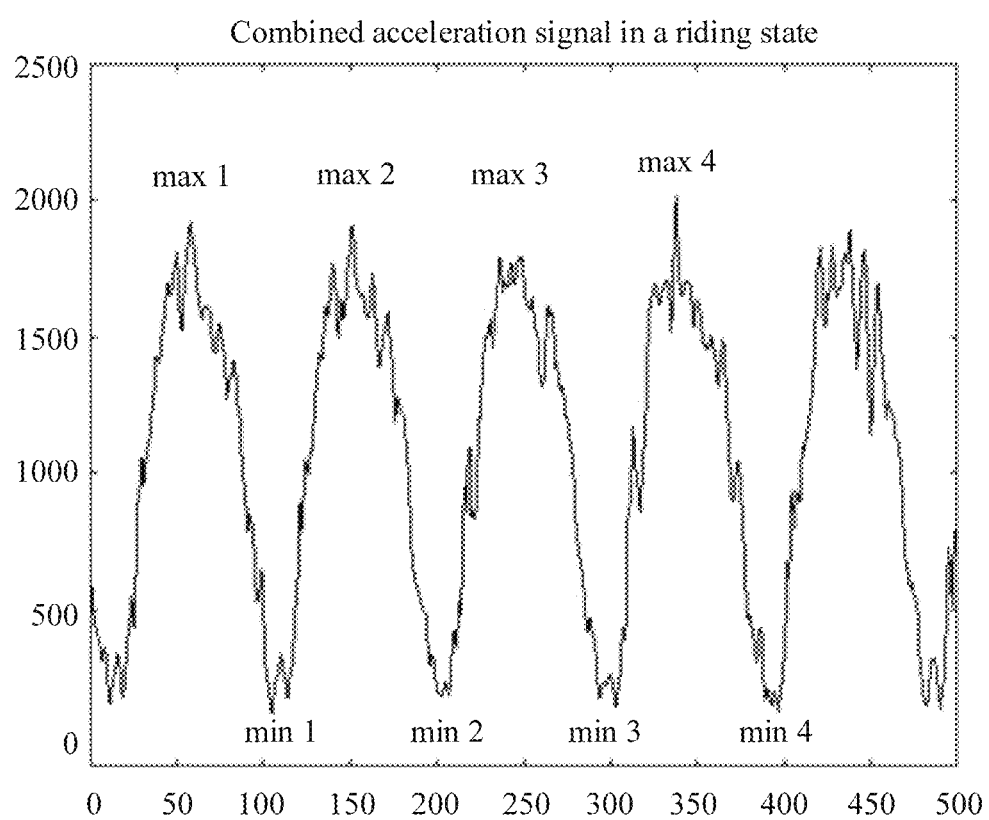
FIG. 3b is a schematic diagram of a combined acceleration signal in a riding state according to an embodiment of this application.
Figure 3C:
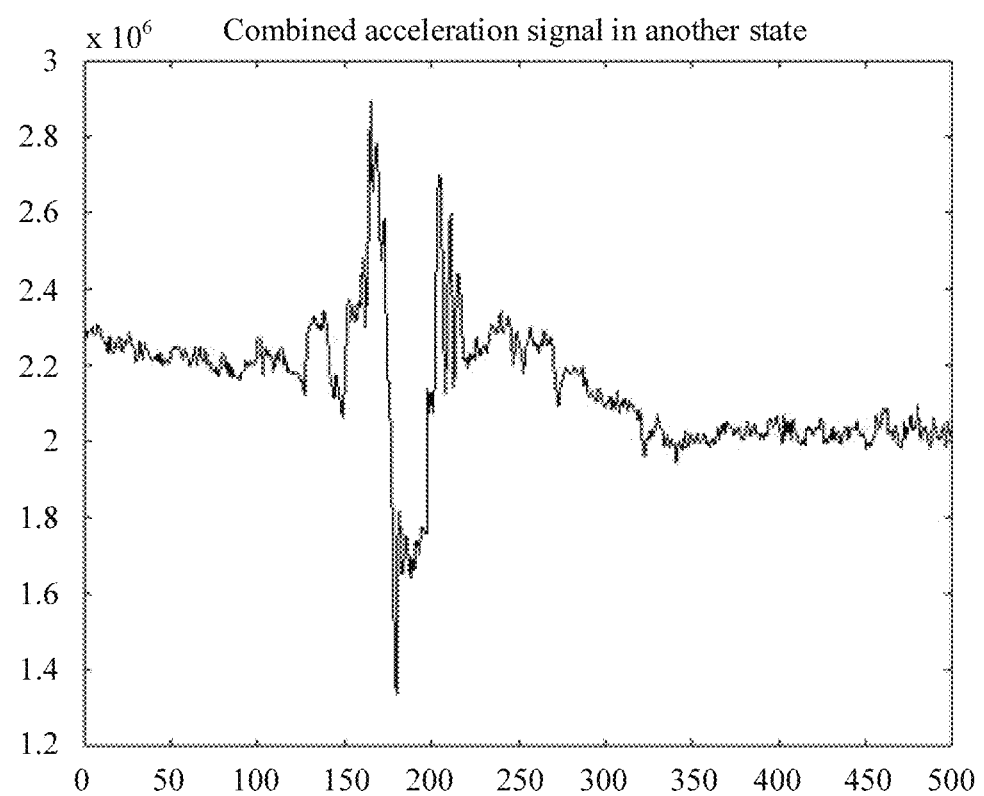
FIG. 3c is a schematic diagram of a combined acceleration signal in another state according to an embodiment of this application.

For example, the first state of the acceleration signal in the first time window may be a static state, a running state, and a walking state shown in FIG. 3*a*, or may be a riding state shown in FIG. 3*b*, or may be another state shown in FIG. 3*c*. For example, for the riding state shown in FIG. 3*b*, extreme value points max 1, max 2, max 3, max 4, min 1, min 2, min 3, and min 4 are characterized by periodic time distribution. The first state is determined based on the combined acceleration, so that a state of the three-axis acceleration signal in the first time window can be preliminarily determined and screened.

In some implementations, it is considered that the three-axis acceleration signal includes a signal that is really needed for calculating the tread frequency and a signal that is not needed. In this embodiment of this application, to accurately calculate the tread frequency and reduce calculation complexity of the tread frequency, a main-axis signal may be selected from the three-axis acceleration signal as the acceleration signal used to calculate the tread frequency. Oscillation is generated during riding of a user wearing a wearable device, and irregular noise caused by the oscillation exists in a three-axis direction. However, there is almost no needed signal of an axis in a direction from the user's left to right. Therefore, a gravity axis acceleration signal in the three-axis acceleration signal may be used as the acceleration signal. It can be learned that only an acceleration signal of an axis in a gravity direction is used. This helps reduce impact caused by the noise and reduce processing difficulty. For example, if a length of the first time window is 5 s, and the sampling frequency is 100 Hz, the signal of each axis has 500 time points and the corresponding amplitude values (namely, the acceleration values). The acceleration values of the 500 time points are averaged to obtain an average value and a standard deviation. An acceleration signal of each axis in the three-axis acceleration signal has one average value and one standard deviation in the first time window. An acceleration signal of one axis may be selected as the main-axis signal based on three average values and three standard deviations.

Then, whether a main-axis acceleration signal is smooth is determined based on a quantity of extreme value points of the combined acceleration. If the main-axis acceleration signal is not smooth, smoothing processing is performed on the main-axis acceleration signal in a moving average filtering manner. Whether there is a high-frequency interference signal in the main-axis acceleration signal is determined. If there is the high-frequency interference signal, the high-frequency interference signal is removed from the acceleration signal in an infinite impulse response (infinite impulse response digital filter, IIR) Butterworth low-pass filtering manner.

202: When it is determined that the first state includes the riding state, determine a feature point set from the acceleration signal.

Time distribution of a feature point in the feature point set meets a preset periodic distribution condition, and an amplitude meets a related physical rule. For example, for the riding state shown in FIG. 3*b*, the feature points max 1, max 2, max 3, max 4, min 1, min 2, min 3, and min 4 are characterized by periodic time distribution, and amplitude meets the related physical rule.

In some implementations, the feature point set may be an intersection point set, an intersection point in the intersection point set is an intersection point between the acceleration signal and an average value, and the average value is an average value of accelerations at all time points in the acceleration signal. Time distribution of these intersection points meets the preset periodic distribution condition, and amplitude meets the related physical rule.

Alternatively, in some implementations, the feature point set includes a maximum value point set and a minimum value point set, both time distribution of a maximum value point in the maximum value point set and time distribution of a minimum value point in the minimum value point set meet the preset periodic distribution condition, and the amplitude meets the related physical rule.

Figure 4:
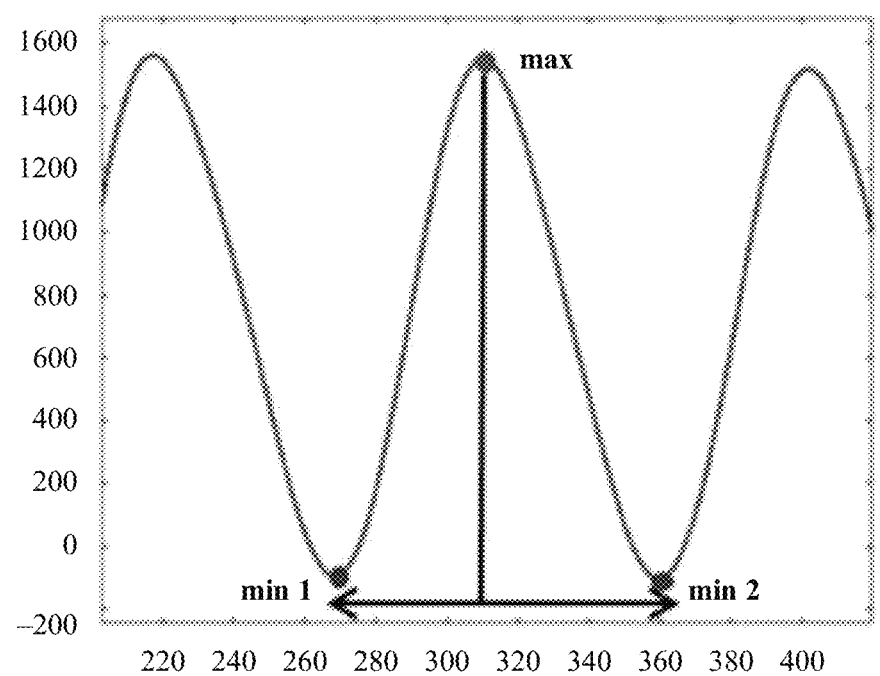
FIG. 4 is a schematic diagram of distribution of extreme value points of a main-axis acceleration signal according to an embodiment of this application.

The extreme value point (including the maximum value point and the minimum value point) is a point whose first-order derivative value is 0, for example, a main-axis acceleration signal shown in FIG. 4. The main-axis acceleration signal includes a maximum value point max and minimum value points min 1 and min 2.

When the maximum value point and the minimum value point are searched in the main-axis acceleration signal, a time interval between two adjacent maximum value points needs to meet a preset time condition, and a maximum value point that meets the time condition is preliminarily obtained through screening. Then, the minimum value point min is found between the two maximum value points. In this way, two time phases of a period are preliminarily found. For the time condition, the time interval between the adjacent maximum value points is usually relatively long. Considering that a time period for a person to ride around is not very short, it may be considered that the time interval is greater than 0.2 s. If the time interval between the two adjacent maximum value points does not meet the time condition, a maximum value point with a larger amplitude value is selected as a candidate maximum value point, and a maximum value point with a smaller amplitude value is discarded. For example, the main-axis acceleration signal shown in FIG. 4 includes the maximum value point max and the minimum value points min 1 and min 2, and one period includes min 1→max 1 and max 1→min 2.

In some implementations, the step of determining the feature point set from the acceleration signal may include step (a) to step (c).

(a) Determine a first maximum value point set and a first minimum value point set from the acceleration signal.

Maximum value points included in the first maximum value point set are all original maximum value points, and minimum value points included in the first minimum value point set are original minimum value points.

(b) Calculate a time ratio and an amplitude ratio, of a first minimum value point and a second minimum value point, relative to a first maximum value point.

The first maximum value point is a maximum value point in the first maximum value point set, both the first minimum value point and the second minimum value are minimum value points in the first minimum value point set, and the first minimum value and the second minimum value are extreme value points adjacent to the first maximum value point.

In some implementations, a calculation formula of the time ratio is $[t(x)-t(y1)]/[t(y2)-t(x)]$, and a calculation formula of the amplitude ratio is $[acc\_f(x)-acc\_f(y1)]/[acc\_f(y2)-acc\_f(x)]$.

In the foregoing, $t(x)$ is a time point corresponding to the first maximum value point x1, $t(y1)$ is a time point corresponding to the first minimum value point y1, $t(y2)$ is a time point corresponding to the second minimum value point y2, $acc\_f(x)$ represents an amplitude value, of the acceleration signal, at x, $acc\_f(y1)$ represents an amplitude value, of the acceleration signal, at y1, and $acc\_f(y2)$ represents an amplitude value, of the acceleration signal, at y2. It should be noted that, if filtering processing is performed on the acceleration signal, when the time ratio and the amplitude ratio are calculated, $acc\_f(x)$, $acc\_f(y1)$, and $acc\_f(y2)$ are all amplitude values of an acceleration signal obtained after the filtering processing. If the filtering processing is not performed on the acceleration signal, when the time ratio and the amplitude ratio are calculated, $acc\_f(x)$, $acc\_f(y1)$, and $acc\_f(y2)$ are all amplitude values of the original acceleration signal. This is not specifically limited in this application.

(c) When the time ratio falls within a first value range and the amplitude ratio falls within a second value range, determine that time distribution of the first maximum value point meets a preset reasonableness condition, which indicates that the first maximum value point is a valid maximum value point. Through step (a) to step (c) in this implementation, reasonableness of maximum value points in the maximum value point set may be determined in sequence, and finally the maximum value point set and the minimum value point set may be obtained.

In some implementations, a preset threshold or an adaptive threshold may be further set to determine reasonableness of the maximum value point in the maximum value point set.

203: When it is determined that a feature point subset in the feature point set meets the preset reasonableness condition, determine that the first state is the riding state.

After the maximum value point set is obtained by determining reasonableness of a single maximum value point, reasonableness of a group of valid maximum value points in the maximum value point set further needs to be determined, to further determine whether the first state in the first time window is the riding state. For determining reasonableness of a group of maximum value points, in some implementations, a condition for determining the reasonableness of the group of valid maximum value points based on a periodic feature of a waveform of the acceleration signal (namely, a principle that parameters change slightly in a period within a short time period) may include the following step (a) to step (e).

(a) Determine based on a first ratio of an average value of the combined acceleration to a quantity of circles. For example, the calculated first ratio (usually, a larger quantity of circles indicates a larger average value) is greater than a first threshold.

(b) On a premise that the time distribution of the maximum value point is even, determine based on a first standard deviation of the time interval between the adjacent maximum value points. The first standard deviation is less than a specified second threshold.

(c) Determine based on a second ratio of a quantity of valid maximum value points to a quantity of original maximum value points. Because there are few invalid maximum value points in the maximum value point set, the second ratio may be set to be greater than a third threshold. Optionally, a value range of the third threshold may be from 0.2 to 0.6. This is not specifically limited in this embodiment of this application.

(d) Determine based on a second standard deviation (an amplitude change is relatively small) of a difference between amplitude values of maximum value points. The second standard deviation is less than a fourth threshold.

(e) Determine based on a relationship between the quantity of circles and a speed range (the relationship is consistent with an initially calculated speed range).

For that a quantity of circles corresponding to a speed less than a first value is not greater than a first quantity of circles, for example, it may be set that the first quantity of circles at a low speed is less than or equal to 4. For a quantity of circles corresponding to a speed greater than the first value and less than a second value is not greater than a second quantity of circles, for example, it may be set that the second quantity of circles at a non-high speed is less than or equal to 8.5. The quantity of circles is a quantity of reasonable periods that are found, and may also be referred to as a quantity of reasonable maximum value points. A specific name is not limited in this application.

It can be learned that, after step (a) to step (e) are performed to determine the reasonableness of the group of valid maximum value points, a range of the valid maximum value points can be further narrowed and be more accurate. This improves data accuracy and further determines whether the first state of the acceleration signal in the first time window is a reasonable riding state.

Optionally, in some embodiments of this application, after it is determined that the first state of the acceleration signal is the riding state, a state in a previous time window further needs to be corrected based on a state of the acceleration signal in the previous time window. In some implementations, three time windows that are adjacent in time domain may be used as an example. A second state of the acceleration signal in a second time window and a third state of the acceleration signal in a third time window are obtained. The second time window, the third time window, and the first time window are adjacent and arranged in ascending order in time domain.

Then, the third state is corrected based on the second state and the first state. For example, when both the second state and the first state are non-riding states, and the third state is the riding state, the state of the acceleration signal in the third time window is corrected to the non-riding state, and a quantity of circles in the third time window is set to 0.

For another example, when both the second state and the first state are riding states, and the third state is the non-riding state, the state of the acceleration signal in the third time window is corrected to the riding state. The second quantity of circles is calculated based on a feature point set of the acceleration signal in the third time window. When a ratio of the second quantity of circles to the first quantity of circles falls within a third value range, it is determined that the state of the acceleration signal in the third time window is the riding state. Because an originally recorded third state is the non-riding state, an originally recorded quantity of circles in the third time window is 0. After the second quantity of circle in the third time window is recalculated this time, a recorded quantity of circles in the third time window may be updated to the second quantity of circle. For example, the quantity of circles may be calculated based on a valid maximum value point in the third time window, and then the quantity of circles in the third time window is compared with a quantity of circles in the first time window. If a ratio is within a specific value range, for example, the ratio is between 0.8 and 1.2, it may be considered that the state in the third time window is the riding state, and the originally recorded quantity 0 of circles in the third time window is replaced with the currently calculated quantity of circles in the third time window.

It can be learned that, after the state in the second time window (namely, the previous time window) is corrected, there may not be a case in which there are two non-riding states and one riding state between the two non-riding states, or a case in which there is another non-static state during riding. It should be noted that states and circles in three consecutive time windows need to be used herein. Therefore, the state in the third time window (namely, a previous time window of the first time window) is corrected in the first time window.

204: Calculate, based on the feature point subset, the quantity of circles and a tread frequency that are in the first time window.

In some implementations, quantity of circles=motion time period×sampling frequency/single-circle period. The motion time period may be in a unit of a time window.

The single-cycle period may be obtained based on a time interval between adjacent feature points. For example, the single-cycle period may be obtained by taking a median from a time interval between adjacent valid maximum value points.

A calculation formula of the tread frequency is: tread frequency=60×sampling frequency/single-circle period× motion time period ratio. The motion time period ratio is a ratio of a time window occupied by an actual riding state to a total motion time period.

In the solution provided in this application, the riding state can be automatically detected. When it is determined that the first state includes the riding state, the feature point set whose time distribution of the feature point meets the preset periodic distribution condition and whose amplitude meets the related physical rule is determined from the acceleration signal. Then, when it is further determined that the feature point subset in the feature point set meets the preset reasonableness condition, it is determined that the first state is the riding state, and then the quantity of circles and the tread frequency that are in the first time window are calculated based on the feature point subset. By using this solution, after the user wears the wearable device on a leg, a quantity of circles and a tread frequency that are of a rotation carrier can be accurately calculated without a need to pre-obtain a parameter of the rotation carrier (for example, the bicycle) or mount the wearable device on the rotation carrier.

Figure 5:
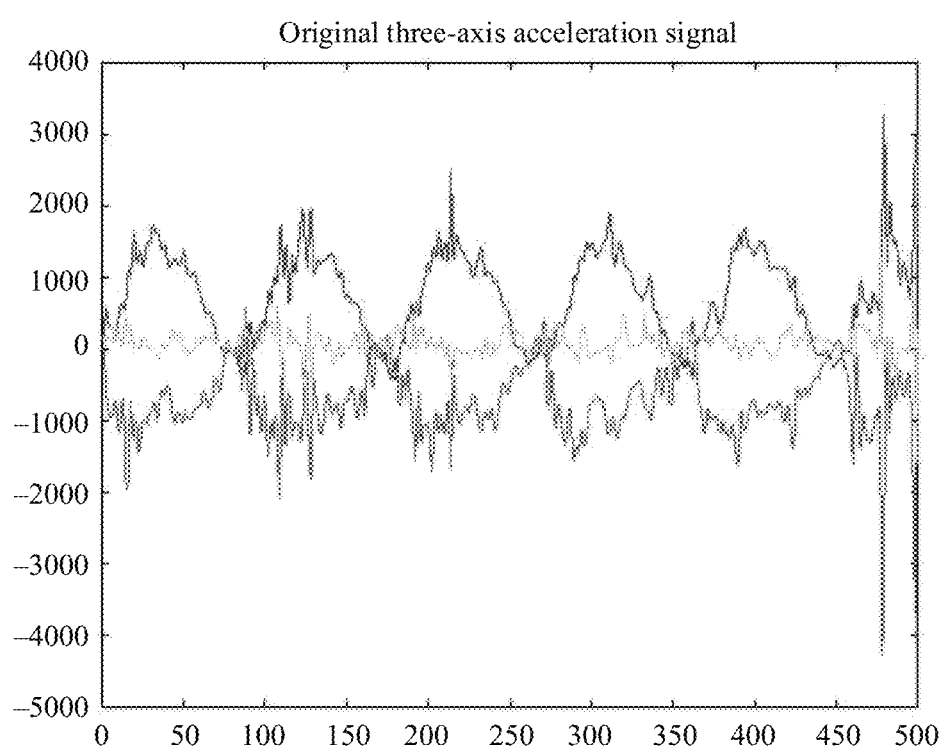
FIG. 5 is a schematic diagram of an original three-axis acceleration signal according to an embodiment of this application.

For ease of understanding, the following uses a stationary bicycle as an example to describe a method for calculating a tread frequency during riding in the embodiments of this application. As shown in FIG. 5, FIG. 5 is a segment of 5-second original acceleration signal input into a wearable device. An acceleration signal, of an axis, with a maximum amplitude average value and a maximum standard deviation is selected from the original acceleration signal shown in FIG. 5 as a main-axis acceleration signal (which may be referred to as a main-axis signal for short). Because noise in the main-axis signal is relatively large, to facilitate subsequent data analysis, in this embodiment of this application, an IIR may be used to perform filtering processing on the main-axis signal. For a main-axis signal obtained after the filtering processing, refer to a schematic diagram of a signal shown in FIG. 6.

Figure 6:
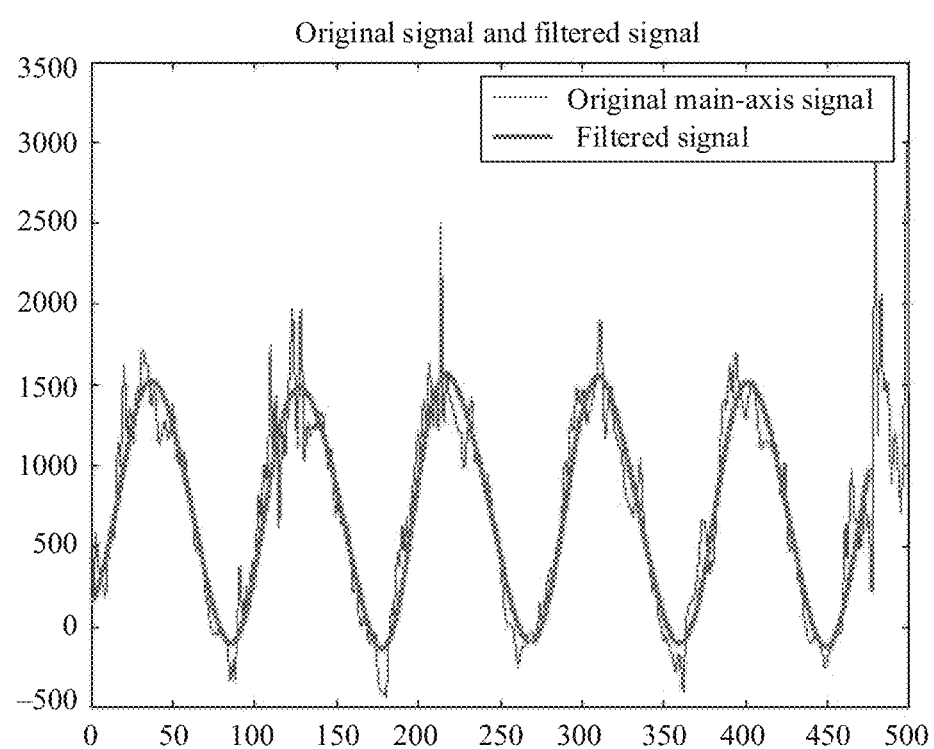
FIG. 6 is a schematic diagram of comparison between an original three-axis acceleration signal and a filtered three-axis acceleration signals according to an embodiment of this application.
Figure 7:
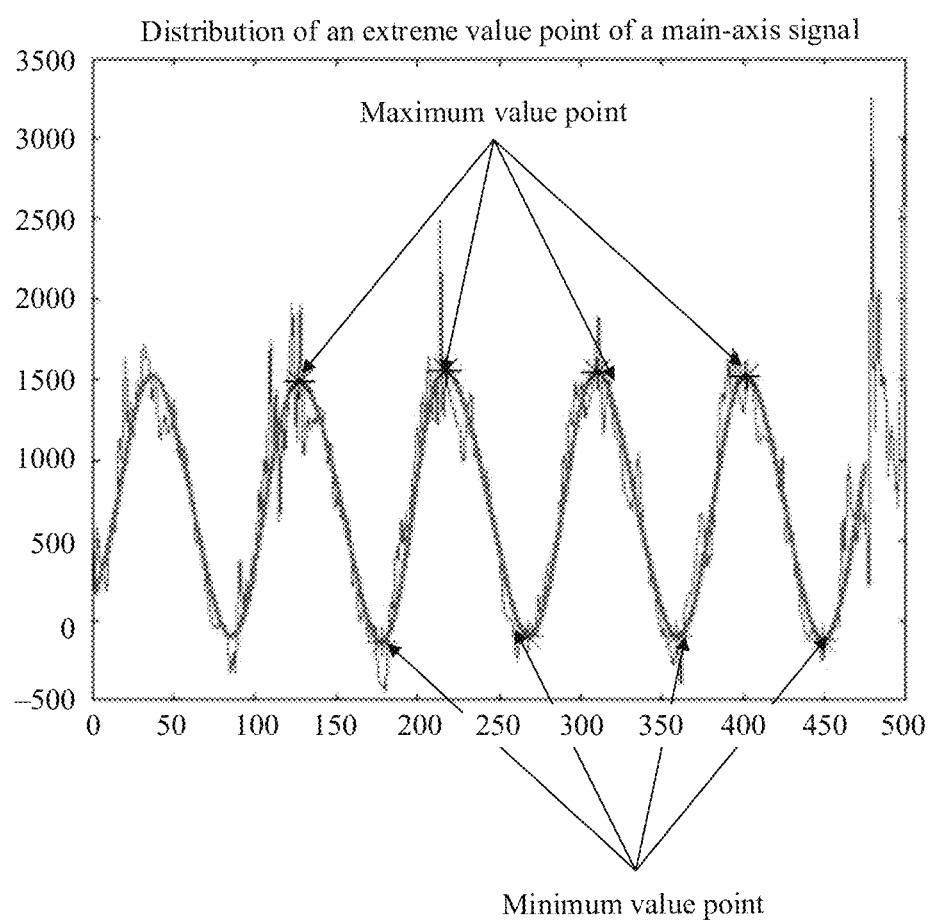
FIG. 7 is a schematic diagram of distribution of extreme value points of a main-axis signal according to an embodiment of this application.

Based on the main-axis signal shown in FIG. 6, a maximum value point and a minimum value point are extracted from the main-axis signal. Finally, four maximum value points and four minimum value points are extracted in total. An extraction result is shown in FIG. 7. As shown in FIG. 7, the four maximum value points whose amplitude values are about 1500 are respectively [127, 217, 310, 401], and the four minimum value points whose amplitude values are about 0 are respectively [178, 268, 359, 449]. The four maximum value points shown in FIG. 7 are all valid maximum value points. For a manner of determining the maximum value point and the minimum value point, refer to the description of step 202 in which the reasonableness of the single maximum value point is determined according to that the time distribution meets the preset reasonableness condition, and refer to the condition, described in step 203, used to determine the reasonableness of the group of valid maximum value points according to step (a) to step (e). A specific determining process is not described herein again. The minimum value point is determined based on the valid maximum value point.

After the four maximum value points and the four minimum value points shown in FIG. 7 are extracted, the following calculates a single-cycle period, a quantity of cycles, and a tread frequency based on a time interval between the maximum value points.

(1) Calculate the single-cycle period. Time intervals between the four maximum value points in FIG. 7 are sequentially [90, 93, 91]. A median 91 is taken from the three time intervals. In other words, the single-cycle period is 91.

(2) Calculate the quantity of circles, where quantity of circles=motion time period x sampling frequency/single-cycle period. For example, if the motion time period is 5 s, the single-cycle period is 91 points, and the sampling frequency is 100 Hz, the quantity of circles is 5×100/91=5.49.

(3) Calculate the tread frequency, where tread frequency=60×sampling frequency/single-cycle period x motion time period ratio=60×100/91×1=65.93.

Figure 8A:
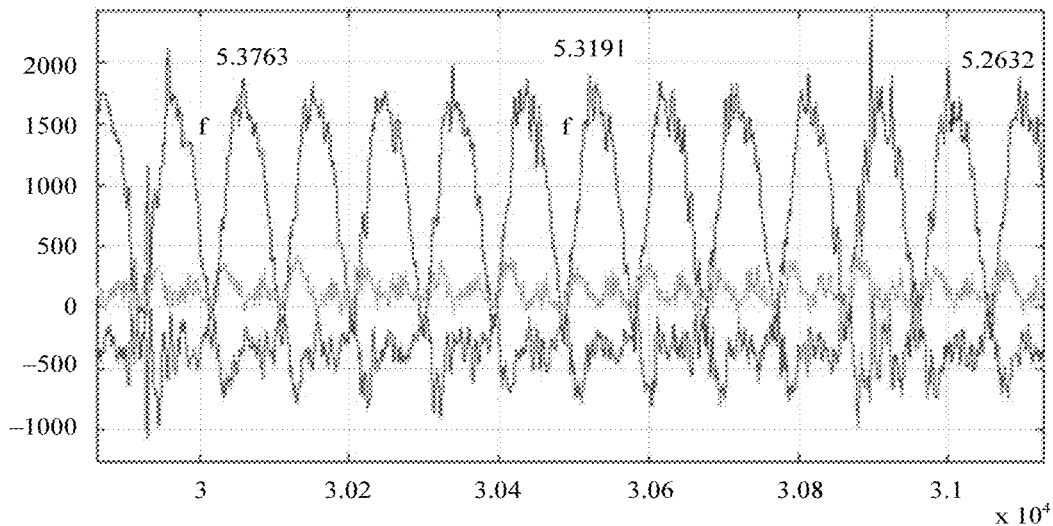
FIG. 8a is a schematic diagram of a riding result of an outdoor bicycle according to an embodiment of this application.
Figure 8B:
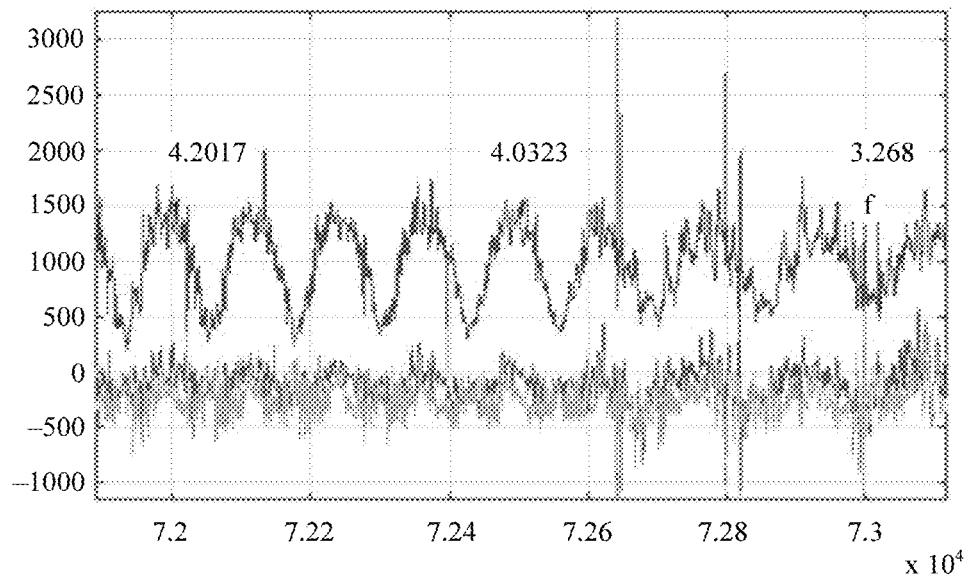
FIG. 8b is a schematic diagram of a riding result of an outdoor bicycle according to an embodiment of this application.
Figure 8C:
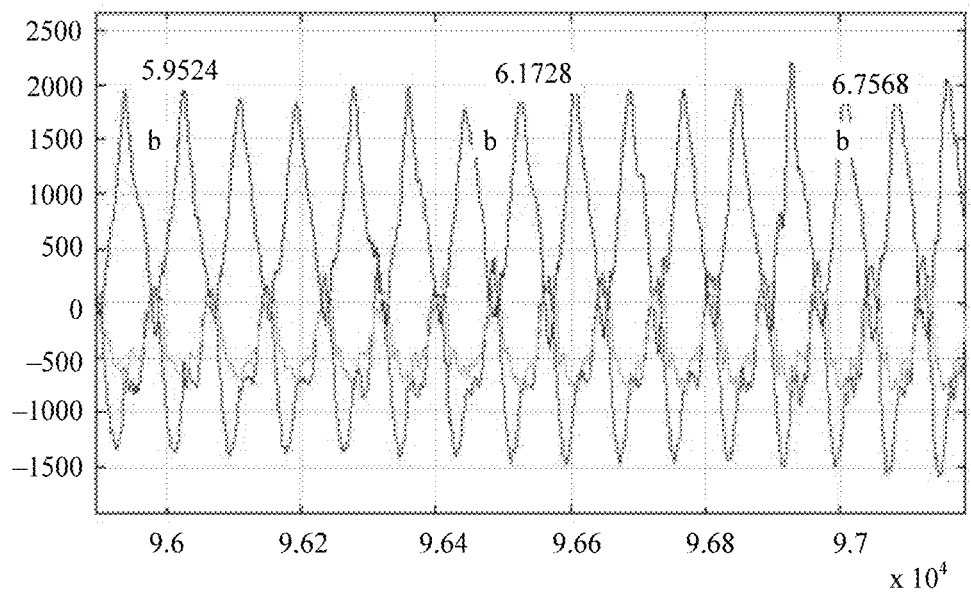
FIG. 8c is a schematic diagram of a riding result of a stationary bicycle according to an embodiment of this application.
Figure 8D:
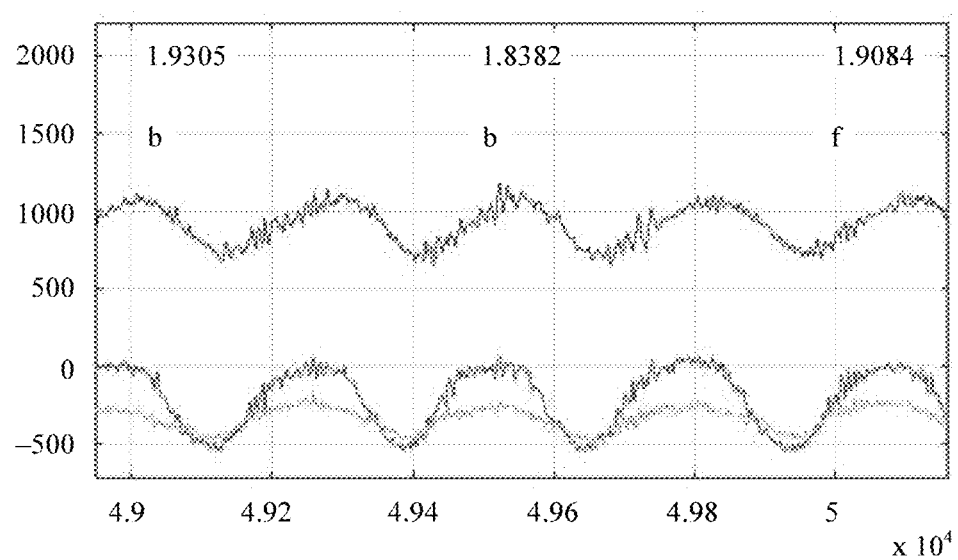
FIG. 8d is a schematic diagram of a riding result of a stationary bicycle according to an embodiment of this application.

Finally, the tread frequency in this time window is 65.93 and the quantity of circles is 5.49. An integer result of the quantity of circles may be displayed. This is not specifically limited in this application. Finally, the quantity of cycles is used for statistics about a riding result of this test. For example, a riding result 1 of an outdoor bicycle is shown in FIG. 8a. According to the solution described in this embodiment of this application, a riding result 2 of the outdoor bicycle, a riding result 1 of a stationary bicycle, and a riding result 2 of the stationary bicycle shown in FIG. 8b to FIG. 8d may be further obtained.

It can be learned that in this embodiment of this application, the quantity of cycles and the tread frequency are accurately calculated by identifying a riding state. If a total quantity of circles is used for the statistics, a final data accuracy can reach 97.66%.

In some implementations, a calculation formula of the accuracy may be accuracy=1—abs (method statistics in the present invention—real quantity of circles)/real quantity of circles. In the foregoing, abs indicates that an absolute value is taken. According to a preliminary experiment, when an experiment condition is that 20 people ride the bicycle and the stationary bicycle, the accuracy on a bicycle side is about 92%, and the accuracy on a stationary bicycle side is 94%. A proportion of a case in which a non-riding state is incorrectly determined as the riding state to a total data duration is less than 0.5%.

Figure 9:
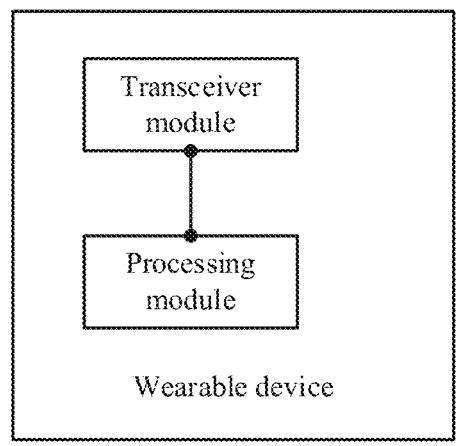
FIG. 9 is a schematic structural diagram of a wearable device according to an embodiment of this application.

The foregoing describes the method for calculating a tread frequency of a bicycle in this application. The following describes a wearable device that performs the method for calculating a tread frequency of a bicycle. Referring to FIG. 9, the wearable device is described. The wearable device includes:

an obtaining module, configured to obtain a first state of an acceleration signal in a first time window; and a processing module, configured to: when it is determined that the first state obtained by the obtaining module includes a riding state, determine a feature point set from the acceleration signal, where time distribution of a feature point in the feature point set meets a preset periodic distribution condition; when it is determined that a feature point subset in the feature point set meets a preset reasonableness condition, determine that the first state is the riding state; and calculate, based on the feature point subset, a quantity of circles and a tread frequency that are in the first time window.

In this embodiment of this application, when it is determined that the first state includes the riding state, the processing module determines, from the acceleration signal, the feature point set whose time distribution of the feature point meets the preset periodic distribution condition and whose amplitude meets a related physical rule. Then, when it is further determined that the feature point subset in the feature point set meets the preset reasonableness condition, it is determined that the first state is the riding state, and then the quantity of circles and the tread frequency that are in the first time window are calculated based on the feature point subset. By using this solution, after a user wears the wearable device on a leg, a quantity of circles and a tread frequency that are of a rotation carrier can be accurately calculated without a need to pre-obtain a parameter of the rotation carrier (for example, the bicycle) or mount the wearable device on the rotation carrier.

Optionally, in some embodiments of this application, the obtaining module is configured to:

obtain a three-axis acceleration signal;

calculate a combined acceleration of acceleration signals, of all axes, in the three-axis acceleration signal; and determine the first state based on the combined acceleration.

Optionally, in some embodiments of this application, the feature point set includes a maximum value point set and a minimum value point set, both time distribution of a maximum value point in the maximum value point set and time distribution of a minimum value point in the minimum value point set meet the preset periodic distribution condition, and the amplitude meets the related physical rule.

Optionally, in some embodiments of this application, the processing module is configured to:

determine a first maximum value point set and a first minimum value point set from the acceleration signal;

calculate a time ratio and an amplitude ratio, of a first minimum value point and a second minimum value point, relative to a first maximum value point, where the first maximum value point is a maximum value point in the first maximum value point set, both the first minimum value point and the second minimum value are minimum value points in the first minimum value point set, and the first minimum value and the second minimum value are extreme value points adjacent to the first maximum value point; and when the time ratio falls within a first value range and the amplitude ratio falls within a second value range, determine that time distribution of the first maximum value point meets the preset reasonableness condition, and obtain the maximum value point set and the minimum value point set.

In some implementations, the time ratio is $[t(x)-t(y1)]/[t(y2)-t(x)]$, and the amplitude ratio is $[acc\_f(x)-acc\_f(y1)]/[acc\_f(y2)-acc\_f(x)]$, where $t(x)$ is a time point corresponding to the first maximum value point x1, $t(y1)$ is a time point corresponding to the first minimum value point y1, $t(y2)$ is a time point corresponding to the second minimum value point y2, $acc\_f(x)$ represents an amplitude value, of the acceleration signal, at x, $acc\_f(y1)$ represents an amplitude value, of the acceleration signal, at y1, and $acc\_f(y2)$ represents an amplitude value, of the acceleration signal, at y2.

In some implementations, after obtaining the maximum value point set and the minimum value point set, the processing module is further configured to:

select a group of maximum value points from the maximum value point set; and determine reasonableness of the group of maximum value points based on the preset reasonableness condition, where the preset reasonableness condition includes at least one of the following items:

a first ratio of an average value of the combined acceleration to a quantity of circles is greater than a first threshold; or a first standard deviation of a time interval between adjacent maximum value points is less than a second threshold; or a second ratio of a quantity of valid maximum value points to a quantity of original maximum value points is greater than a third threshold; or a second standard deviation of a difference between amplitude values of maximum value points is less than a fourth threshold; or a quantity of circles corresponding to a speed less than a first value is not greater than a first quantity of circles, a quantity of circles corresponding to a speed greater than the first value and less than a second value is not greater than a second quantity of circles, and the first quantity of circles is less than the second quantity of circles.

Optionally, in some embodiments of this application, after determining that the first state of the acceleration signal is the riding state, the processing module is further configured to:

obtain, through the obtaining module, a second state of the acceleration signal in a second time window and a third state of the acceleration signal in a third time window, where the second time window, the third time window, and the first time window are adjacent and arranged in ascending order in time domain; and correct the third state based on the second state and the first state.

Optionally, in some embodiments of this application, the processing module is configured to:

when both the second state and the first state are non-riding states, and the third state is the riding state, correct the state of the acceleration signal in the third time window to the non-riding state, and set a quantity of circles in the third time window to 0; or when both the second state and the first state are riding states, and the third state is a non-riding state, correct the state of the acceleration signal in the third time window to the riding state.

Optionally, in some embodiments of this application, when both the second state and the first state are the riding states, and the third state is the non-riding state, the processing module is further configured to:

calculate the second quantity of circles based on a feature point set of the acceleration signal in the third time window; and when a ratio of the second quantity of circles to the first quantity of circles falls within a third value range, determine that the state of the acceleration signal in the third time window is the riding state, and update a recorded quantity of circles in the third time window to the second quantity of circles.

Figure 10:
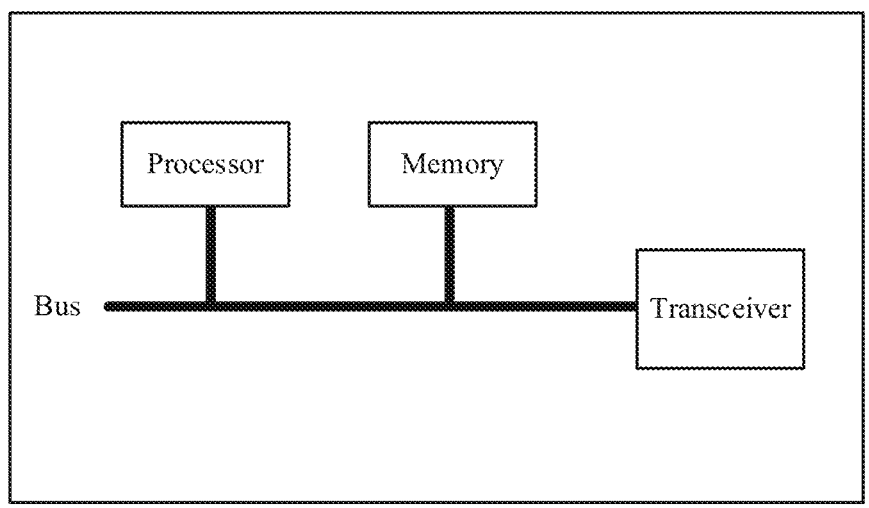
FIG. 10 is a schematic structural diagram of a wearable device according to an embodiment of this application.

FIG. 10 is another schematic structural diagram of a wearable device according to an embodiment of this application. The wearable device may include at least one processor, at least one network interface or another communications interface, a memory, at least one communications bus, and at least one transceiver that are configured to implement connection and communication between these apparatuses. The processor is configured to execute an executable module stored in the memory, for example, a computer program. The memory may include a high speed random access memory (English full name: Random Access Memory, RAM for short), or may further include a non-volatile memory (non-volatile memory), for example, at least one magnetic disk memory. A communication connection between a system gateway and at least one another network element is implemented through the at least one network interface (which may be a wired interface or a wireless interface), and the internet, a wide area network, a local area network, a metropolitan area network, or the like may be used.

As shown in FIG. 10, in some implementations, the memory stores a program instruction, and the program instruction may be executed by the processor. The program instruction stored in the memory is invoked, so that the processor specifically executes program code that needs to be invoked when the service management method in the embodiments of this application is performed.

It should be noted that in the embodiment corresponding to FIG. 9 of this application, a physical device corresponding to the transceiver module may be the transceiver, and a physical device corresponding to the processing module may be the processor. Each apparatus shown in FIG. 9 may have a structure shown in FIG. 10. When one of the apparatuses has the structure shown in FIG. 10, the processor and the transceiver in FIG. 10 implement functions same as or similar to those of the processing module and the transceiver module that are provided in the foregoing apparatus embodiment corresponding to the apparatus, and the memory in FIG. 10 stores program code that needs to be invoked when the processor performs the method for calculating a tread frequency of a bicycle.

This application further provides a computer storage medium. The medium stores a program. When the program is executed, some or all of the steps in the method, for calculating a tread frequency of a bicycle, performed by the wearable device are included.

In the foregoing embodiments, a description of each embodiment has respective focuses. For a part that is not described in detail in an embodiment, refer to related descriptions in another embodiment.

A person skilled in the art may be clearly understood that, for convenient and brief description, for a detailed working process of the foregoing system, apparatus, and unit, refer to a corresponding process in the foregoing method embodiment. Details are not described herein again.

In the several embodiments provided in this application, it should be understood that the disclosed system, apparatus, and method may be implemented in another manner. For example, the described apparatus embodiment is merely an example. For example, division into the modules or units is merely logical function division and may be other division in an actual implementation. For example, a plurality of modules or components may be combined or integrated into another system, or some features may be ignored or not performed. In addition, the displayed or discussed mutual coupling or a direct coupling or a communication connection may be implemented by using some interfaces. An indirect coupling or a communication connection between the apparatuses or units may be implemented in an electronic form, a mechanical form, or in another form.

The modules described as separate parts may or may not be physically separate, and parts displayed as modules may or may not be physical modules, may be located in one position, or may be distributed on a plurality of network modules. Some or all of the modules may be selected based on an actual requirement to achieve the objectives of the solutions in the embodiments.

In addition, functional modules in the embodiments of this application may be integrated into one processing module, or each of the modules may exist alone physically, or two or more modules are integrated into one module. The integrated module may be implemented in a form of hardware, or may be implemented in a form of a software function module. When the integrated module is implemented in the form of a software function module and sold or used as an independent product, the integrated module may be stored in a computer-readable storage medium.

All or some of the foregoing embodiments may be implemented through software, hardware, firmware, or any combination thereof. When software is used to implement the embodiments, all or some of the embodiments may be implemented in a form of a computer program product.

The computer program product includes one or more computer instructions. When the computer program instructions are loaded and executed on a computer, the procedures or the functions according to the embodiments of this application are all or partially generated. The computer may be a general-purpose computer, a special-purpose computer, a computer network, or another programmable apparatus. The computer instructions may be stored in the computer-readable storage medium or may be transmitted from one computer-readable storage medium to another computer-readable storage medium. For example, the computer instructions may be transmitted from one website, computer, server, or data center to another website, computer, server, or data center wiredly (for example, a coaxial cable, an optical fiber, or a digital subscriber line (DSL)) or wirelessly (for example, infrared, radio, or microwave). The computer-readable storage medium may be any usable medium accessible by a computer, or a data storage device, for example, a server or a data center, integrating one or more usable media. The usable medium may be a magnetic medium (for example, a floppy disk, a hard disk, or a magnetic tape), an optical medium (for example, a DVD), a semiconductor medium (for example, a solid-state drive Solid State Disk (SSD)), or the like.

The technical solutions provided in this application are described in detail above. The principle and implementation of this application are described herein through specific examples. The description about the embodiments is merely provided to help understand the method and core ideas of this application. In addition, a person of ordinary skill in the art can make variations to the specific implementations and application scopes according to the idea of this application. Therefore, the content of specification shall not be construed as a limit to this application.

What is claimed is:

1. A method for calculating a tread frequency of a bicycle implemented by a wearable device, wherein the method comprises:
    obtaining a first state of an acceleration signal in a first time window;
    determining a feature point set from the acceleration signal, wherein a time distribution of a feature point in the feature point set meets a preset periodic distribution condition, and wherein an amplitude of the feature point meets a physical rule;
    determining that the first state is a riding state when a feature point subset in the feature point set meets a preset condition; and
    calculating, based on the feature point subset, a quantity of circles and a tread frequency that are in the first time window.

2. The method of claim 1, further comprising:
    obtaining a three-axis acceleration signal;
    calculating a combined acceleration of acceleration signals of all axes in the three-axis acceleration signal; and
    obtaining the first state based on the combined acceleration.

3. The method of claim 2, wherein the acceleration signal is a gravity axis acceleration signal in the three-axis acceleration signal.

4. The method of claim 2, further comprising:
    determining a first maximum value point set and a first minimum value point set from the acceleration signal;
    calculating a time ratio and an amplitude ratio of a first minimum value point and a second minimum value point relative to a first maximum value point, wherein the first maximum value point is a maximum value point in the first maximum value point set, wherein both the first minimum value point and the second minimum value point are minimum value points in the first minimum value point set, and wherein the first minimum value point and the second minimum value point are extreme value points adjacent to the first maximum value point;
    determining that a time distribution of the first maximum value point meets the preset condition when the time ratio falls within a first value range and the amplitude ratio falls within a second value range; and
    obtaining the maximum value point set and the minimum value point set.

5. The method of claim 4, further comprising:
    selecting a group of maximum value points from the maximum value point set; and
    determining a reasonableness of the group of maximum value points based on the preset condition, wherein the preset condition comprises at least one of:
        a first ratio of an average value of the combined acceleration to a quantity of circles is greater than a first threshold;
        a first standard deviation of a time interval between adjacent maximum value points is less than a second threshold;
        a second ratio of a quantity of valid maximum value points to a quantity of original maximum value points is greater than a third threshold;
        a second standard deviation of a difference between amplitude values of maximum value points is less than a fourth threshold; or
        a quantity of circles corresponding to a first speed less than a first value is less than or equal to a first quantity of circles, a quantity of circles corresponding to a second speed greater than the first value and less than a second value is less than or equal to a second quantity of circles, and the first quantity of circles is less than the second quantity of circles.

6. The method of claim 5, further comprising:
    obtaining a second state of the acceleration signal in a second time window and a third state of the acceleration signal in a third time window, wherein the second time window, the third time window, and the first time window are adjacent and arranged in ascending order in a time domain; and
    correcting the third state based on the second state and the first state.

7. The method of claim 6, wherein when both the second state and the first state are non-riding states and the third state is the riding state, the method further comprises:
    correcting the third state to the non-riding state; and
    setting a quantity of circles in the third time window to zero.

8. The method of claim 6, further comprising correcting the third state to the riding state when both the second state and the first state are riding states and the third state is a non-riding state.

9. The method of claim 8, further comprising:
    calculating the second quantity of circles based on a second feature point set of the acceleration signal in the third time window when both the second state and the first state are the riding state and the third state is the non-riding state;
    determining that the third state is the riding state when a ratio of the second quantity of circles to the first quantity of circles falls within a third value range; and
    updating a recorded quantity of circles in the third time window to the second quantity of circles.

10. The method of claim 1, wherein the feature point set is an intersection point set, wherein an intersection point in the intersection point set is an intersection point between the acceleration signal and an average value, and wherein the average value is an average value of accelerations at all time points in the acceleration signal.

11. A computer program product comprising computer-executable instructions stored on a non-transitory computer readable medium that, when executed by a processor, cause a wearable device to:
    obtain a first state of an acceleration signal in a first time window;
    determine a feature point set from the acceleration signal, wherein a time distribution of a feature point in the feature point set meets a preset periodic distribution condition, and wherein an amplitude of the feature point meets a physical rule;

determine that the first state is a riding state when a feature point subset in the feature point set meets a preset condition; and calculate, based on the feature point subset, a quantity of circles and a tread frequency that are in the first time window.

12. The computer program product of claim 11, wherein the computer-executable instructions further cause the wearable device to:

obtain a three-axis acceleration signal;

calculate a combined acceleration of acceleration signals of all axes in the three-axis acceleration signal; and obtain the first state based on the combined acceleration.

13. The computer program product of claim 12, wherein the acceleration signal is a gravity axis acceleration signal in the three-axis acceleration signal.

14. The computer program product of claim 12, wherein the computer-executable instructions further cause the wearable device to:

determine a first maximum value point set and a first minimum value point set from the acceleration signal;

calculate a time ratio and an amplitude ratio of a first minimum value point and a second minimum value point relative to a first maximum value point, wherein the first maximum value point is a maximum value point in the first maximum value point set, wherein both the first minimum value point and the second minimum value point are minimum value points in the first minimum value point set, and wherein the first minimum value point and the second minimum value point are extreme value points adjacent to the first maximum value point;

determine that a time distribution of the first maximum value point meets the preset condition when the time ratio falls within a first value range and the amplitude ratio falls within a second value range; and obtain the maximum value point set and the minimum value point set.

15. The computer program product of claim 14, wherein the computer-executable instructions further cause the wearable device to:

select a group of maximum value points from the maximum value point set; and determine a reasonableness of the group of maximum value points based on the preset condition, wherein the preset condition comprises at least one of:

a first ratio of an average value of the combined acceleration to a quantity of circles is greater than a first threshold;

a first standard deviation of a time interval between adjacent maximum value points is less than a second threshold;

a second ratio of a quantity of valid maximum value points to a quantity of original maximum value points is greater than a third threshold;

a second standard deviation of a difference between amplitude values of maximum value points is less than a fourth threshold; or a quantity of circles corresponding to a first speed less than a first value is less than or equal to a first quantity of circles, a quantity of circles corresponding to a second speed greater than the first value and less than a second value is less than or equal to a second quantity of circles, and the first quantity of circles is less than the second quantity of circles.

16. The computer program product of claim 15, wherein the computer-executable instructions further cause the wearable device to:

obtain a second state of the acceleration signal in a second time window and a third state of the acceleration signal in a third time window, wherein the second time window, the third time window, and the first time window are adjacent and arranged in ascending order in a time domain; and correct the third state based on the second state and the first state.

17. The computer program product of claim 16, wherein when both the second state and the first state are non-riding states and the third state is the riding state, the computer-executable instructions further cause the wearable device to:

correct the third state to the non-riding state; and set a quantity of circles in the third time window to zero.

18. The computer program product of claim 16, wherein the computer-executable instructions further cause the wearable device to correct the third state to the riding state when both the second state and the first state are riding states and the third state is a non-riding state.

19. The computer program product of claim 18, wherein the computer-executable instructions further cause the wearable device to:

calculate the second quantity of circles based on a second feature point set of the acceleration signal in the third time window when both the second state and the first state are the riding state and the third state is the non-riding state;

determine that the third state is the riding state when a ratio of the second quantity of circles to the first quantity of circles falls within a third value range; and update a recorded quantity of circles in the third time window to the second quantity of circles.

20. The computer program product of claim 11, wherein the feature point set is an intersection point set, wherein an intersection point in the intersection point set is an intersection point between the acceleration signal and an average value, and wherein the average value is an average value of accelerations at all time points in the acceleration signal.

* * * * *